(12) United States Patent
Doyon

(10) Patent No.: US 10,827,731 B2
(45) Date of Patent: Nov. 10, 2020

(54) METHOD OF INACTIVATING THE IPK1 GENE IN CORN

(71) Applicant: Sangamo Therapeutics, Inc., Richmond, CA (US)

(72) Inventor: Yannick Doyon, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 0 days.

(21) Appl. No.: 15/990,176

(22) Filed: May 25, 2018

(65) Prior Publication Data

US 2018/0263228 A1    Sep. 20, 2018

Related U.S. Application Data

(63) Continuation of application No. 12/806,396, filed on Aug. 11, 2010, now abandoned.

(60) Provisional application No. 61/273,928, filed on Aug. 11, 2009.

(51) Int. Cl.
| | |
|---|---|
| *C12N 15/00* | (2006.01) |
| *A01K 67/027* | (2006.01) |
| *C12N 15/82* | (2006.01) |
| *C12N 15/85* | (2006.01) |

(52) U.S. Cl.
CPC ...... *A01K 67/0276* (2013.01); *C12N 15/8213* (2013.01); *C12N 15/8509* (2013.01)

(58) Field of Classification Search
USPC ........ 435/325; 800/278, 260, 265, 266, 267, 800/270, 300, 300.1, 320.1
See application file for complete search history.

(56) References Cited

U.S. PATENT DOCUMENTS

| | | | |
|---|---|---|---|
| 4,425,737 A * | 1/1984 | Henke ............... | A01H 1/04 47/DIG. 1 |
| 5,356,802 A | 10/1994 | Chandrasegaran | |
| 5,420,032 A | 5/1995 | Marshall et al. | |
| 5,436,150 A | 7/1995 | Chandrasegaran | |
| 5,464,764 A | 11/1995 | Capecchi et al. | |
| 5,487,994 A | 1/1996 | Chandrasegaran | |
| 5,658,772 A * | 8/1997 | Odell ............... | C07K 14/32 435/320.1 |
| 5,789,538 A | 8/1998 | Rebar et al. | |
| 5,925,523 A | 7/1999 | Dove et al. | |
| 5,968,793 A | 10/1999 | Liu et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas et al. | |
| 6,200,759 B1 | 3/2001 | Dove et al. | |
| 6,242,568 B1 | 6/2001 | Barbas et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,534,261 B1 | 3/2003 | Cox et al. | |
| 6,833,252 B1 | 12/2004 | Dujon et al. | |
| 6,903,185 B2 | 6/2005 | Kim et al. | |
| 7,153,949 B2 | 12/2006 | Kim et al. | |
| 7,267,979 B2 | 9/2007 | Yadev | |
| 2003/0232410 A1 | 12/2003 | Liljedahl et al. | |
| 2004/0002092 A1 | 1/2004 | Arnould et al. | |
| 2005/0026157 A1 | 2/2005 | Baltimore et al. | |
| 2005/0064474 A1 | 3/2005 | Urnov et al. | |
| 2005/0208489 A1 | 9/2005 | Carroll et al. | |
| 2006/0063231 A1 | 3/2006 | Li et al. | |
| 2006/0078552 A1 | 4/2006 | Arnould et al. | |
| 2006/0153826 A1 | 7/2006 | Arnould et al. | |
| 2006/0188987 A1 | 8/2006 | Guschan et al. | |
| 2006/0206949 A1 | 9/2006 | Arnould et al. | |
| 2007/0117128 A1 | 5/2007 | Smith et al. | |
| 2007/0134796 A1 | 6/2007 | Holmes et al. | |
| 2007/0218528 A1 | 9/2007 | Miller et al. | |
| 2008/0131962 A1 | 6/2008 | Miller | |
| 2008/0182332 A1 | 7/2008 | Cai et al. | |
| 2008/0299580 A1 | 12/2008 | DeKelver et al. | |
| 2009/0068164 A1 | 3/2009 | Segal et al. | |
| 2009/0111188 A1 | 4/2009 | Cai et al. | |
| 2009/0117617 A1 | 5/2009 | Holmes et al. | |
| 2009/0263900 A1 | 10/2009 | DeKelver et al. | |
| 2010/0003756 A1 | 1/2010 | Collingwood et al. | |

FOREIGN PATENT DOCUMENTS

| | | |
|---|---|---|
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |

(Continued)

OTHER PUBLICATIONS

Shukla (Nature Letters, May 21, 2009, vol. 459, p. 437-441 and Supplemental Materials).*
Wright (Plant J., 2005, 44, p. 693-705).*
Maeder (Mol. Cell. Jul. 25, 2008, vol. 31, Nol. 2, p. 294-301.*
Lloyd (PNAS, Feb. 8, 2005, vol. 102, No. 6, p. 2232-2237).*
Schuler (Genetics, Nov. 1954, vol. 39, p. 908-922).*
Cooley (Plant Mol. Biol. 1998, vol. 38, p. 521-530).*
Dinges (Plant Physiology, S001, vol. 125, No. 3, p. 1406-1418).*
Shen (PNAS, May 27, 2003, vol. 100, No. 11, p. 6552-6557).*
Chen ("Increased insulin and leptin sensitivity in mice lacking acyl CoA:diacylglycerol acyltransferase" J. Clin. Invest., 2002, vol. 109, p. 1049-1055).*

(Continued)

*Primary Examiner* — Michael C Wilson
(74) *Attorney, Agent, or Firm* — Dahna S. Pasternak; Pasternak Patent Law

(57) ABSTRACT

Disclosed herein are homozygously modified organisms and methods of making and using these organisms.

4 Claims, 4 Drawing Sheets

Specification includes a Sequence Listing.

(56) References Cited

FOREIGN PATENT DOCUMENTS

| WO | WO 01/60970 A2 | 8/2001 |
|----|----------------|--------|
| WO | WO 01/88197 A2 | 11/2001 |
| WO | WO 02/016536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 07/014275 A2 | 1/2007 |
| WO | WO 07/139898 A2 | 12/2007 |
| WO | WO 09/042163 A2 | 4/2009 |

OTHER PUBLICATIONS

Gisler (Plant J., 2002, vol. 32, No. 3, p. 277-284).*
Gisler, et al., "The Role of Double-Strand Break-Induced Allelic Homologous Recombination in Somatic Plant Cells," The Plant Journal 32(3): 277-284 (2002).
Argast, et al., "I-PPOI and I-CREI Homing Site Sequence Degeneracy Determined by Random Mutagenesis and Sequential In Vitro Enrichment," J. Mol. Biol. 280:345-353 (1998).
Arnould, et al., "Engineering of Large Numbers of Highly Specific Homing Endonucleases That Induce Recombination on Novel DNA Targets," J Mol Biol 355:443-458 (2006).
Ashworth, et al., "Computational Redesign of Endonuclease DNA Binding and Cleavage Specificity,"Nature 441:656-659 (2006).
Beerli, et al., "Engineering Polydactyl Zinc-Finger Transcription Factors," Nature Biotechnology 20:135-141 (2002).
Belfort, et al., "Homing Endonucleases: Keeping the House in Order," Nucleic Acids Research 25:3379-3388 (1997).
Beumer, et al., "Efficient Gene Targeting in Drosophila With Zinc-Finger Nucleases," Genetics 172:2391-2403 (2006).
Bibikova, et al., "Stimulation of Homologous Recombination Through Targeted Cleavage by Chimeric Nucleases," Mol. Cell Biol. 21:289-297 (2001).
Bibikova, et al., "Targeted Chromosomal Cleavage and Mutagenesis in Drosophilia Using Zinc-Finger Nucleases," Genetics 161(3): 1169-1175 (2002).
Bitinate, et al., "Foki Dimerization Is Required for DNA Cleavage," PNAS USA 95:10570-10575 (1998).
Boch, et al., "Breaking the Code of DNA Binding Specificity of TAL-Type III Effectors," Science 326:1509-1512 (2009).
Bonas, et al., "Genetic and Structural Characterization of the Avirulence Gene AVRBS3 From Xanthomonas Campestris Pv. Vesicatoria," Mol Gen Genet 218:127-136 (1989).
Carbery, et al., "Targeted Genome Modification in Mice Using Zinc-Finger Nucleases," Genetics 186:451-459 (2010).
Carroll, et al., "Progress and Prospects: Zinc-Finger Nucleases Gene Therapy Agents," Gene Therapy 15:1463-1468 (2008).
Chames, et al., "In Vivo Selection of Engineered Homing Endonucleases Using Double-Strand Break Induced Homologous Recombination," Nuc Acids Res 33:e178 (2005).
Chen, et al., "Increased Insulin and Leptin Sensitivity in Mice Lacking Acyl COA:Diacylglycerol Acyltransferase 1,"J. Clin Invest 109: 1049-1055 (2002).
Chevalier, et al., "Design, Activity, and Structure of a Highly Specific Artificial Endonuclease," Molecular Cell 10:895-905 (2002).
Chilton, et al., "Targeted Integration of T-DNA Into the Tobacco Genome at Double-Stranded Breaks: New Insights on the Mechanism of T-DNA Integration," Plant Physiology 133:956-965 (2003).
Choo, et al., "Advances in Zinc Finger Engineering," Curr. Opin. Struct. Biol. 10:411-416 (2000).
Christian, et al., "TAL Effector Nucleases Create Targeted DNA Double Strand Breaks," Genetics 2010; published ahead of print on Jul. 26, 2010 as doi: 10.1534/genetics.110.120717 (2010).
Christian, et al., "Targeting DNA Double-Strand Breaks With TAL Effector Nucleases," Genetics 186:757-761 (2010).
Cohen-Tannoudji, et al., "I-SCEL-Inducted Gene Replacement at a Natural Locus in Embryonic Stem Cells," Molecular and Cellular Biology 18:1444-1448 (1998).

Cooley, et al., "Insertional Inactivation of the Tomato Polygalacturonase Gene," Plant Mol Biol 38(4): 521-530 (1998).
Deutsch, et al., "Intron-Exon Structures of Eukaryotic Model Organisms," Nucleic Acids Research 27(15): 3219-3228 (1999).
Dinges, et al, "Molecular Structure of Three Mutations at the Maizesugaryi Locus and Their Allele-Specific Phenotypic Effects," Plant Physiology 125(3): 1406-1418 (2001).
Donoho, et al., "Analysis of Gene Targeting and Intrachromosomal Homologous Recombination Stimulated by Genomic Double-Strand Breaks in Mouse Embryonic Stem Cells," Mol. and Cell. Biol. 18: 4070-4078 (1998).
Doyon, et al., "Heritable Targeted Gene Disruption in Zebrafish Using Designed Zinc-Finger Nucleases," Nature Biotechnology 26:702-708 (2008).
Dujon, et al., "Mobile Introns: Definition of Terms and Recommended Nomenclature," Gene 82:115-118 (1989).
Durai, et al., "Zinc Finger Nucleases: Custom-Designed Molecular Scissors for Genome Engineering of Plant and Mammalian Cells," Nucleic Acids Research 33(18):5978-5990 (2005).
Epinat, et al., "A Novel Engineered Meganuclease Induces Homologous Recombination in Yeast and Mammalian Cells," Nucleic Acids Research 31:2952-2962 (2003).
Geurts, et al., "Knockout Rats via Embryo Microinjection of Zinc-Finger Nucleases," Science 325:433 (2009).
Gimble, et al., "Substrate Recognition and Induced DNA Distortion by the PI-SCEI Endonuclease, an Enzyme Generated by Protein Splicing," J. Mol. Biol. 263:163-180 (1996).
Gouble, et al., "Efficient in TOTO Targeted Recombination in Mouse Liver by Meganuclease-Induced Double-Strand Break," J Gene Med 8:616-622 (2006).
Govindarajan, et al., "Intracorneal Positioning of the Lens in PAX6-GAL4/VP16 Transgenic Mice," Molecular Vision 11:876-886 (2005).
Hauschild, et al., "Efficient Generation of a Biallelic Knockout in Pigs Using Zinc-Finger Nucleases," PNAS 108:12013-12017 (2011).
Heuer, et al., "Repeat Domain Diversity of AVRBS3-Like Genes in Ralstonia Solanacearum Strains and Association With Host Preferences in the Field," Appl and Envir Micro 73:4379-4384 (2007).
Hugnet, et al.,"Frequency of the Mutant MDR1 Allele Associated With Multidrug Sensitivity in a Samlple of Collies From France," Journal of Veterinary Pharmacology and Therapeutics 27(4):227-229 (2004).
Isalan et al., "A Rapid, Generally Applicable Method to Engineer Zinc Fingers Illustrated by Targeting the HIV-1 Promoter," Nat Biotechnol 19:656-660 (2001).
Jasin, et al., "Genetic Manipulation of Genomes With Rare-Cutting Endonucleases," Trends Genet 12:224-228 (1996).
Kandevelou, et al., "Targeted Manipulation of Mammalian Genomes Using Designed Zinc Finger Nucleases," Biochemical and Biophysical Research Communication 388(1): 56-61 (2009).
Kay, et al., "A Bacterial Effector Acts as a Plant Transcription Factor and Induces a Cell Size Regulator," Science 318:648-651 (2007).
Kim, et al., "Chimeric Restriction Endonuclease," PNAS USA 91:883-887 (1994).
Kim, et al., "Insertion and Deletion Mutants of POKI Restriction Endonuclease," J. Biol. Chem. 269:31978-31981 (1994).
Kooraneef, et al., "Naturally Occurring Genetic Variation in Arabidopsis thaliana," Annu Rev Plant Biol 55:141-172 (2004).
Leneuve, et al., "Genotyping of CRE-LOX Mice and Detection of Tissue-Specific Recombination by Multiplex PCR," BioTechniques 31:1156-1162 (2001).
Li, et al., "Functional Domains in FOK I Restriction Endonuclease," PNAS USA 89:4275-4279 (1992).
Li, et al., "Alteration of the Cleavage Distance of FOK I Restriction Endonuclease by Insertion Mutagenesis," PNAS USA 90:2764-2768 (1993).
Liang, et al., "Establishment of a Patterned GAL4-VP16 Transactivation System for Discovering Gene Function in Rice," The Plant Journal 46:1059-1072 (2006).
Lin, et al., "Neurological Abnormalities in a Knock-In Mouse Model of Huntington's Disease," Human Molecular Genetics 10(2): 137-144 (2001).

(56) References Cited

OTHER PUBLICATIONS

Lloyd, A. et al., "Targeted Mutagenesis Using Zinc-Finger Nucleases in *Arabidopsis,*" *Proc. Natl Acad. Sci. USA* 102:2232-2237 (2005).
Maeder. et al., "Rapid "Open-Source" Engineering of Customized Zincfinger Nucleases for Highly Efficient Gene Modification," *Mol. Cell* 21:294-301 (2008).
Map of pCAMIAB2300 (2006).
Meng, et al., "Targeted Gene Inactivation in Zebrafish Using Engineered Zinc-Finger Nucleases," *Nat Biotech* 26:695-701 (2008).
Miller, et al., "An Improved Zinc-Finger Nuclease Architecture for Highly Specific Genome Editing," *Nature Biotech* 25:778-785 (2007).
Monnat, et al., "Generation of Highly Site-Specific DNA Double-Strand Breaks in Human Cells by the Homing Endonucleases I-PPOJ and I-CREI," *Biochem Biophysics Res Common* 255:88-93 (1999).
Moraveiková, et al., "Feasibility of the Seed Specific Cruciferin C Promoter in the Self Excision CRE/LOXP Strategy Focused on Generation of Marker-Free Transgenic Plants," *Theor. Appl. Genet.* 117(8):1325-1334 (2008); doi: 10.1007/s00122-008-0866-4.
Morton, et al., "Induction and Repair of Zinc-Finger Nuclease-Targeted Double-Strand Breaks in Caenorhabditis Elegans Somatic Cells," *PNAS* 13:16370-16375 (2006).
Moscou, et al., "A Simple Cipher Governs DNA Recognition by TAL Effectors," *Science* 326:1501 (2009).
Pabo, et al., "Design and Selection of Novel CYS2-HIS2 Zinc Finger Proteins," *Ann. Rev. Biochem*, 70:313-340 (2001).
Paques, et al., "Meganucleases and DNA Double-Strand Break-Induced Recombination: Perspectives for Gene Therapy," *Current Gene Therapy* 7:49-66 (2007).
Peilberg, et al., "A CIS-Acting Regulatory Mutation Causes Premature Hair Graying and Susceptibility to Melanoma in the Horse," Nature Genetics 40(8):1004-1009 (2008).
Perez, et al., "Establishment of HIV-1 Resistance in CD4+ T Cells by Genome Editing Using Zinc-Finger Nucleases," *Nat. Biotech.* 26(7):808-816 (2008).
Perler, et al., "Protein Splicing Elements: Inteins and Exteins a Definition of Terms and Recommended Nomenclature," *Nucleic Acids Research* 22:1125-1127 (1994).
Porteus, et al., "Gene Targeting Using Zinc Finger Nucleases," *Nature Biotechnology* 23:967-973 (2005).
Puchta, et al., "Two Different but Related Mechanisms Are Used in Plants for the Repair of Genomic Double-Strand Breaks by Homologous Recombination," *PNAS USA* 93:5055-5060 (1996).
Pulkkinen "Homozygous Deletion Mutations in the Plectin Gene (PLECI) in Patients With Epidermolysis Bullosa Simplex Associated With Late-Onset Muscular Dystrophy," *Human Molecular Genetics* 5(10): 1539-1546 (1996).
Ramanjuan, "Historic Mutant Corn Garden Grows at Cornell," Cornell Chronicle pp. 1-2 (Jun. 23, 2006).
Rieder, et al., "Mutations in the Agouti (ASID), The Extension (MC1R), and the Brown (TYRPI) Loci and Their Association to Coat Color Phenotypes in Horses (*Equus caballus*)," *Mammalian Genome* 12(6):450-455 (2001).
Roberts, et al., "Rebase: Restriction Enzymes and Methyltransferases," *Nucleic Acids Research* 31:418-420 (2003).
Rong, et al., "Targeted Mutagenesis by Homologous Recombination in *D. Melanogaster*," *Genes & Dev* 16:1568-1581 (2002).
Rouet, et al., "Introduction of Double-Strand Breaks Into the Genome of Mouse Cells by Expression of a Rare-Cutting Endonuclease,"*Molecular and Cellular Biology* 14:8096-8106 (1994).
Schneider, et al., "Generation a Conditional Allele of the Mouse Prostaglandin EP4 Receptor," *Genesis* 9:7-14 (2004).
Schomack, et al., "Gene-for-Gene-Mediated Recognition of Nuclear-Targeted AVRBS3-Like Bacterial Effector Proteins," *J Plant Physiol* 163:256-272 (2006).
Schuler, "Natural Mutations in Inbred Lines of Maize and Their Heterotic Effect. I. Comparison of Parent, Mutant and Their $F_1$ Hybrid in a Highly Inbred Background," *Genetics* 39(6): 908-922 (1954).
Segal, et al., "Custom DNA-Binding Proteins Come of Age: Polydactyl Zinc-Finger Proteins," *Curr. Opin. Biotechnol.* 12:632-637 (2001).
Shen, et al., "SAL1 Determines the Number of Aleurone Cell Layers Maize in Endosperm and Encodes a Class E Vacuolar Sorting Protein," *PNAS* 100(11): 6552-6551(2003).
Shukla, et al., "Precise Genome Modification in the Crop Species *Zea mays* Using Zinc-Finger Nucleases," *Nature* 459:437-441 (2009) including online supplemental materials.
Smith, et al., "Expression of a Truncated Tomato Polygalacturonase Gene Inhibits Expression of the Endogenous Gene in Transgenic Plants," *Mol Gen Genet* 224(3): 477-481 (1990).
Sussman, et al., "Isolation and Characterization of New Homing Endonuclease Specificities at Individual Target Site Positions," *J Mol Biol* 342:31-41 (2004).
Urnov, et al., "Highly Efficient Endogenous Human Gene Correction Using Designed Zinc-Finger Nucleases," *Nature* 435:646-651 (2005).
Vasquez, et al., "Manipulating the Mammalian Genome by Homologous Recombination," PNAS 98:8403-8410 (2001).
Vasquez, et al., "The Nuclear DSRNA Binding Protein HYL1 Is Required for MicroNRA Accumulation and Plant Development, but Not Posttranscriptional Transgene Silencing," *Current Biology* 14(4): 346-351 (2004).
Whitt, et al., "Genetic Diversity and Selection in the Maize Starch Pathway," *PNAS* 99(20): 12959-12962 (2002).
Wisman, et al., "The Behaviour of the: Autonomous Maize Transposable Element EN/SPM in *Arabidopsis thaliana* Allows Efficient Mutagensis," *Plant Molecular Biology* 37:989-999 (1998).
Woods, et al.,"Targeted Mutagenesis in Zebrafish," *Nature Biotechnology* 26(6): 650-651 (2008).
Wright, et al., "High-Frequency Homologous Recombination in Plants Mediated by Zinc-Finger Nucleases," *Plant J.* 44:693-705 (2005).
Wu et al., "Custom-Designed Zinc Finger Nucleases: What Is Next?," *Cell. Mol. Life Sci.* 64:2933-2944 (2007).

* cited by examiner

FIGURE 1

```
WT IPK1 -> CCAACACCTGGCTGCCAATCATCTCGATGGTGGGTGGGTATGGT
           CCAACACCTGGGTG:: :: :: :: ::TGTCGATGGTGGGTGGGTATGGT
           CCAACACCTGGGTG:: :: :: :: ::TGTCGATGGTGGGTGGGTATGGT
           CCAACACCTGGGTG:: :: :: :: ::TGTCGATGGTGGGTGGGTATGGT
           CCAACACCTGGGTG:: :: :: :: ::TGTCGATGGTGGGTGGGTATGGT
```

FACS and Southern blot confirmation of heterozygous H3.3B-EYFP ES cells

ES cell Negative Control
~0.0% of sorted cells meeting size criteria are EYFP+ (1/100,000)

H3.3B-EYFP ES cells
~1-1.6% of sorted cells meeting size criteria are EYFP+

-WT – probe recognizes 11,663bp
-Integrated – probe recognizes 7973 bp

Figure 4: Non-reporter mouse HB3.3

```
GCCCAAAGACATCCAGTTGGCTCG--------CCGGATACGGGGGAGAGAGAGCT  wildtype
GCCCAAAGACAT----------------------CCGGATACGGGGGAGAGAGAGCT  <--NHEJ
GCCCAAAGACATCCAGTTGGCTCG----------CCGGATACGGGGGAGAGAGAGCT
GCCCAAAGACATCCAG------------------ACATTTTGGGGGAGAGAGAGCT  <--NHEJ
GCCCAAAGACATCCAGNTGGCTCG----------CCAGATACNNGGGAGANAGCT   <--NHEJ
GCCCAAAGACATCCAGTTGGCTCG----------CCGGATACNGGGGAGAGAGAGCT
GCCCAAAGACATCCAGTTGGCTCG----------CCGGATACGGGGGAGAGAGAGCT
GCCCAAAGACATCCAGTTGGCTCG----------CCGGATACGGGGGAGAGAGAGCT
GCCCAAAGACATCCAGTTGGCTCG----------CCGGATACGGGGGAGAGAGAGCT
GCCCAAAGACATCCAGTTGGCTCG----------CCGGATACGGGGGAGAGAGAGCT
GCCCAAAGACATCCAGTTGGCTCG----------CCGGATACGGGGGAGAGAGAGCT
GCCCAAAGACATCCAGTTGGCTCG----------CCGGATACGGGGGAGAGAGAGCT
GCCCAAAGACATCCAGTTGGCTCGCTCGCCG---CCGGATACGGGGGAGAGAGAGCT <--NHEJ
GCCCAAAGACATCCAGTTGGCTGGC---------CGGATACGGNGGGAGAGAGAGCT <--NHEJ
GCCCAAAGACATCCAGTTGGCTCG----------CCGGATACGGGGGAGAGAGAGCT
GCCCAAAGACATCCAGTTGGCTCG----------CCGGATACGGGGGAGAGAGAGCT
GCCCAAAGACATCCAGTTGGCTCG----------CCGGATACGGGGGAGAGAGAGCT
GCCCAAAGACATCCAGTTGGCTCG----------CCGGATACGGGGGAGAGAGAGCT
GCCCAAAGACATCCAGTTG---------------CCGGATACGGGGGAGAGAGAGCT <--NHEJ
GCCCAAAGACATCCAGTTG---------------CCGGATACGGGGGAGAGAGAGCT <--NHEJ
```

US 10,827,731 B2

SEQUENCE LISTING

```
<160> NUMBER OF SEQ ID NOS: 23

<210> SEQ ID NO 1
<211> LENGTH: 7
<212> TYPE: PRT
<213> ORGANISM: Mus sp.

<400> SEQUENCE: 1

Arg Ser Asp His Leu Ser Glu
1               5

<210> SEQ ID NO 2
<211> LENGTH: 7
<212> TYPE: PRT
<213> ORGANISM: Mus sp.

<400> SEQUENCE: 2

Arg Asn Asp Thr Arg Lys Thr
1               5

<210> SEQ ID NO 3
<211> LENGTH: 7
<212> TYPE: PRT
<213> ORGANISM: Mus sp.

<400> SEQUENCE: 3

Gln Ser Ser Asn Leu Ala Arg
1               5

<210> SEQ ID NO 4
<211> LENGTH: 7
<212> TYPE: PRT
<213> ORGANISM: Mus sp.

<400> SEQUENCE: 4

Arg Ser Asp Asp Arg Lys Thr
1               5

<210> SEQ ID NO 5
<211> LENGTH: 7
<212> TYPE: PRT
```

```
<213> ORGANISM: Mus sp.

<400> SEQUENCE: 5

Asp Arg Ser Ala Leu Ser Arg
1               5

<210> SEQ ID NO 6
<211> LENGTH: 7
<212> TYPE: PRT
<213> ORGANISM: Mus sp.

<400> SEQUENCE: 6

Thr Ser Ala Asn Leu Ser Arg
1               5

<210> SEQ ID NO 7
<211> LENGTH: 7
<212> TYPE: PRT
<213> ORGANISM: Mus sp.

<400> SEQUENCE: 7

Arg Ser Asp Val Leu Ser Glu
1               5

<210> SEQ ID NO 8
<211> LENGTH: 7
<212> TYPE: PRT
<213> ORGANISM: Mus sp.

<400> SEQUENCE: 8

Gln Arg Asn His Arg Thr Thr
1               5

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cgccggatac ggggag                                                    16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gccaactgga tgtctt                                                    16

<210> SEQ ID NO 11
<211> LENGTH: 9
<212> TYPE: PRT
<213> ORGANISM: Unknown
<220> FEATURE:
<223> OTHER INFORMATION: Description of Unknown: LAGLIDADG motif
      sequence

<400> SEQUENCE: 11

Leu Ala Gly Leu Ile Asp Ala Asp Gly
1               5
```

```
<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Arg Pro Val Ala Thr
1               5

<210> SEQ ID NO 13
<211> LENGTH: 41
<212> TYPE: DNA
<213> ORGANISM: Zea mays

<400> SEQUENCE: 13
ccaacacctg ggtgccaatc atgtcgatgg tggggtatgg t                    41

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ccaacacctg ggtgtgtcga tggtggggta tggt                            34

<210> SEQ ID NO 15
<211> LENGTH: 46
<212> TYPE: DNA
<213> ORGANISM: Mus sp.

<400> SEQUENCE: 15
gcccaaagac atccagttgg ctcgccggat acggggggag agagct               46

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcccaaagac atccggatac ggggggagag agct                            34

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gcccaaagac atccagacat tttgggggga gagagct                         37

<210> SEQ ID NO 18
<211> LENGTH: 46
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (33)..(34)
<223> OTHER INFORMATION: a, c, t, g, unknown or other
<220> FEATURE:
<221> NAME/KEY: modified_base
<222> LOCATION: (42)..(42)
<223> OTHER INFORMATION: a, c, t, g, unknown or other

<400> SEQUENCE: 18
gcccaaagac atccagntgg ctcgccagat acnngggag anagct              46

<210> SEQ ID NO 19
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (33)..(33)
<223> OTHER INFORMATION: a, c, t, g, unknown or other

<400> SEQUENCE: 19
gcccaaagac atccagttgg ctcgccggat acnggggag agagct              46

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gcccaaagac atccagttgg ctcgctcgcc ggatacgggg ggagagagct         50

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: a, c, t, g, unknown or other

<400> SEQUENCE: 21
gcccaaagac atccagttgg ccggatacgg ngggagagag ct                 42

<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gcccaaagac atccagttgc cggatacggg gggagagagc t                  41
```

```
<210> SEQ ID NO 23
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gcccaaagac atccagttgc cggatacggg gggagagagc t                        41
```

METHOD OF INACTIVATING THE IPK1 GENE IN CORN

CROSS-REFERENCE TO RELATED APPLICATIONS

The present application is a continuation of U.S. patent application Ser. No. 12/806,396, filed Aug. 11, 2010, which claims the benefit of U.S. Provisional Application No. 61/273,928, filed Aug. 11, 2009, the disclosures of which are hereby incorporated by reference in their entireties.

STATEMENT OF RIGHTS TO INVENTIONS MADE UNDER FEDERALLY SPONSORED RESEARCH

Not applicable.

TECHNICAL FIELD

The present invention relates to organisms which are homozygous for targeted modification of one or more endogenous genes. More specifically, the invention concerns organisms (e.g., plants or animals) in which both alleles of a gene are disrupted but in which the homozygous knockout organism does not contain exogenous sequences at the disrupted locus. The invention also concerns organisms (e.g., plants or animals) in which both alleles of a gene are modified by insertion of a transgene, wherein the transgene lacks sequences encoding a reporter (e.g., selectable marker).

BACKGROUND

Organisms (e.g., plants and animals) with homozygous targeted gene modifications are useful in a wide variety of agricultural, pharmaceutical and biotechnology applications. These organisms have traditionally been generated by inducing homologous recombination of a desired sequence (donor) at the gene selected for modification. However, in order to select for cells which have the incorporated the donor DNA into the targeted locus, the targeting vector must include both positive and negative selection markers. See, e.g., U.S. Pat. No. 5,464,764. The selected cells produce heterozygotes that must be crossed to obtain organisms homozygous for the gene modification. Throughout the process, the selection markers remain integrated in the organism's genome such that the resulting modified homozygote includes both the modified gene and exogenous (e.g., marker) sequences.

Recently, nucleases, including zinc finger nucleases and homing endonucleases such as I-SceI, that are engineered to specifically bind to target sites have been successfully used for genome modification in a variety of different species. See, for example, United States Patent Publications 20030232410; 20050208489; 20050026157; 20050064474; 20060188987; 20060063231; 2008/0182332; 2009/0111188, and International Publication WO 07/014275, the disclosures of which are incorporated by reference in their entireties for all purposes. These ZFNs can be used to create a double-strand break (DSB) in a target nucleotide sequence, which increases the frequency of donor nucleic acid introduction via homologous recombination at the targeted locus (targeted integration) more than 1000-fold. In addition, the inaccurate repair of a site-specific DSB by non-homologous end joining (NHEJ) can also result in targeted gene disruption.

Nonetheless, as with non-nuclease methods, in order to readily identify nuclease-mediated modifications in many organisms, an exogenous DNA including a selection marker or reporter gene is also targeted to the selected locus. See, e.g., Shukla et al. (2009) Nature 459(7245):437-441; U.S. Patent Publication Nos. 2008/0182332 and 2009/0111188. While targeted integration of a reporter allows for identification of modifications for a number of applications, this technique is not always desirable as it leaves additional exogenous nucleic acid sequences inserted into the genome.

Thus, there remains a need for compositions and methods for generating homozygous organisms modified at a desired gene locus, including homozygous KO organisms without inserted exogenous sequences at the locus (loci) targeted for modification and homozygous transgenic organisms without sequences encoding reporters such as selectable markers.

SUMMARY

Described herein are homozygous organisms comprising a modification at a desired gene locus as well as methods and systems for generating these organisms. Modified organisms include homozygous KO organisms without inserted exogenous sequences at the locus (loci) targeted for modification and homozygous transgenic organisms without sequences encoding reporters (e.g., selectable markers).

In one aspect, provided herein is a modified organism comprising at least one gene locus in which both alleles of the locus are modified (e.g., disrupted), but wherein the modified organism does not comprise exogenous sequences at the modified locus. In other embodiments, the organisms as described herein may comprise one or more transgenes (exogenous sequences) at any locus that is not disrupted (knocked out).

In another aspect, provided herein is a modified organism comprising at least one gene locus in which both alleles of the locus comprise a transgene, wherein the transgene does not comprise a reporter such as a screening or selectable marker. In a further aspect, provided herein is a modified organism comprising at least one gene locus in which all alleles (e.g., in a tri- or tetraploid organism) of the locus comprise a transgene, wherein the transgene does not comprise a reporter such as a screening or selectable marker.

Any of the organisms described herein may comprise more than one bi-allelic (or multi-allelic) modification (e.g., disruption or transgene). Furthermore, the organism may be for example, a eukaryote (e.g., a plant or an animal such as a mammal, such as a rat, mouse, or fish).

In yet another aspect, provided herein is a method of generating a homozygous (bi-allelic) knockout organism lacking exogenous sequences, the method comprising, introducing an exogenous sequence (e.g., reporter) into a cell using a nuclease that mediates targeted integration of the exogenous sequence into a selected locus of the genome, identifying cells in which the exogenous sequence has been introduced into one allele of the target locus (mono-allelic TI cells), identifying mono-allelic TI cells comprising a NHEJ deletion at the other allele (TI/NHEJ clones), allowing the TI/NHEJ clones to develop to reproductive maturity, crossing the TI/NHEJ organisms to each other (or in the case of plants, also allowing the organism to "self"), and identifying progeny that exhibit bi-allelic NHEJ modifications, thereby generating a bi-allelic knockout organism lacking exogenous sequences at the target locus. In yet another aspect, provided herein is a method of generating a homozygous (bi-allelic) organism comprising desired transgene sequences lacking sequences encoding a reporter (e.g., selectable marker), the method comprising, introducing an exogenous reporter sequence into a cell using a nuclease that mediates targeted integration of the reporter exogenous sequence into a selected locus of the genome, introducing the desired transgene sequence(s) into a cell wherein the nuclease mediates targeted integration of the transgene sequence into the selected locus of the genome, identifying cells in which the exogenous reporter sequence has been introduced into one allele of the target locus (mono-allelic reporter-TI cells), identifying mono-allelic reporter-TI cells comprising a transgene insertion at the other allele (reporter-TI/transgene clones), allowing the reporter-TI/transgene clones to develop to reproductive maturity, crossing the reporter-TI/transgene organisms to each other (or in the case of plants, also allowing the organism to "self"), and identifying progeny that exhibit bi-allelic transgene insertions, thereby generating a bi-allelic organism comprising the desired transgene but lacking reporter sequences at the target locus.

In certain embodiments, the nuclease comprises one or more zinc finger nucleases (ZFN). In other embodiments, the nuclease comprises a homing endonuclease or meganuclease, or a TAL-effector domain nuclease fusion ("TALEN"). In any of the embodiments described herein, the exogenous sequence (e.g., exogenous reporter sequence) and transgene may be introduced concurrently or sequentially with the nuclease(s). In some aspects, the exogenous sequence comprises a reporter gene such as a selectable marker (e.g., an herbicide resistant gene for plants) or a screening marker (e.g. a fluorescent protein). Any of the methods described herein may be repeated to generate organisms that are homozygous KOs or contain homozygous transgene insertions at multiple loci. It will be apparent that any of the methods described herein can be applied to polyploid organisms (e.g., by repeating the steps) that include more than two alleles, for example, tri- or tetraploid plants.

In another aspect, the invention provides kits that are useful for generating organisms with homozygous targeted gene modifications without inserted reporter (e.g screening or selection) sequences. The kits typically include one or more nucleases (or polynucleotides encoding the nuclease) that bind to a target site (the selected locus for modification), optional cells containing the target site(s) of the nuclease, an exogenous sequence for targeted integration, an optional donor transgene comprising sequences homologous to the target site, and instructions for (i) introducing the nucleases and exogenous sequence into the cells; (ii) identifying cells into which the exogenous sequences are inserted into an allele at the target locus; (iii) identifying cells having mono-allelic targeted integration of the exogenous reporter sequence and modifications at the other allele of the locus (reporter-TI/modified cells); (iv) growing/developing selected cells into reproductively mature organisms; (v) crossing the reporter-TI/modified heterozygous organisms; (vi) identifying progeny of the reporter-TI/modified crosses that are bi-allelic for the targeted gene modification. These steps may be repeated in polyploid organisms to modify all alleles as desired.

BRIEF DESCRIPTION OF THE DRAWINGS

FIG. 1 depicts sequence analysis of the non-TI allele of a ZFN-TI-modified IPK1 chromatid from *Zea mays*. The sequences are shown in SEQ ID NO: 13 and SEQ ID NO: 14. Underlined base pairs show the binding sites for ZFN pair used for genomic modifications. The ":" indicate deleted bases. The wild-type sequence is indicated in the first line and the multiple sequence reads of the sequenced non-TI allele event are shown below.

FIG. 3A depicts the FACS results of ES cells lacking the inserted EYFP gene sequence in the H3.3B locus (top panel) and those results for cells that received the H3.3B-EYFP insertion. FIG. 3B depicts a Southern blot derived from genomic DNA of cells that have the inserted H3.3B-EYFP sequence versus wildtype cells.

FIG. 4 depicts the sequences from 19 non-reporter alleles (SEQ ID NOs:15-23) demonstrating NHEJ in the H3.3B-EYFP/heterozygotes. Underlined base pairs show the binding sites for the ZFN pair used for the modifications. The "-" indicate deleted bases or spaces in the sequence to allow for alignment with the clones containing insertions.

DETAILED DESCRIPTION

Figure 2:
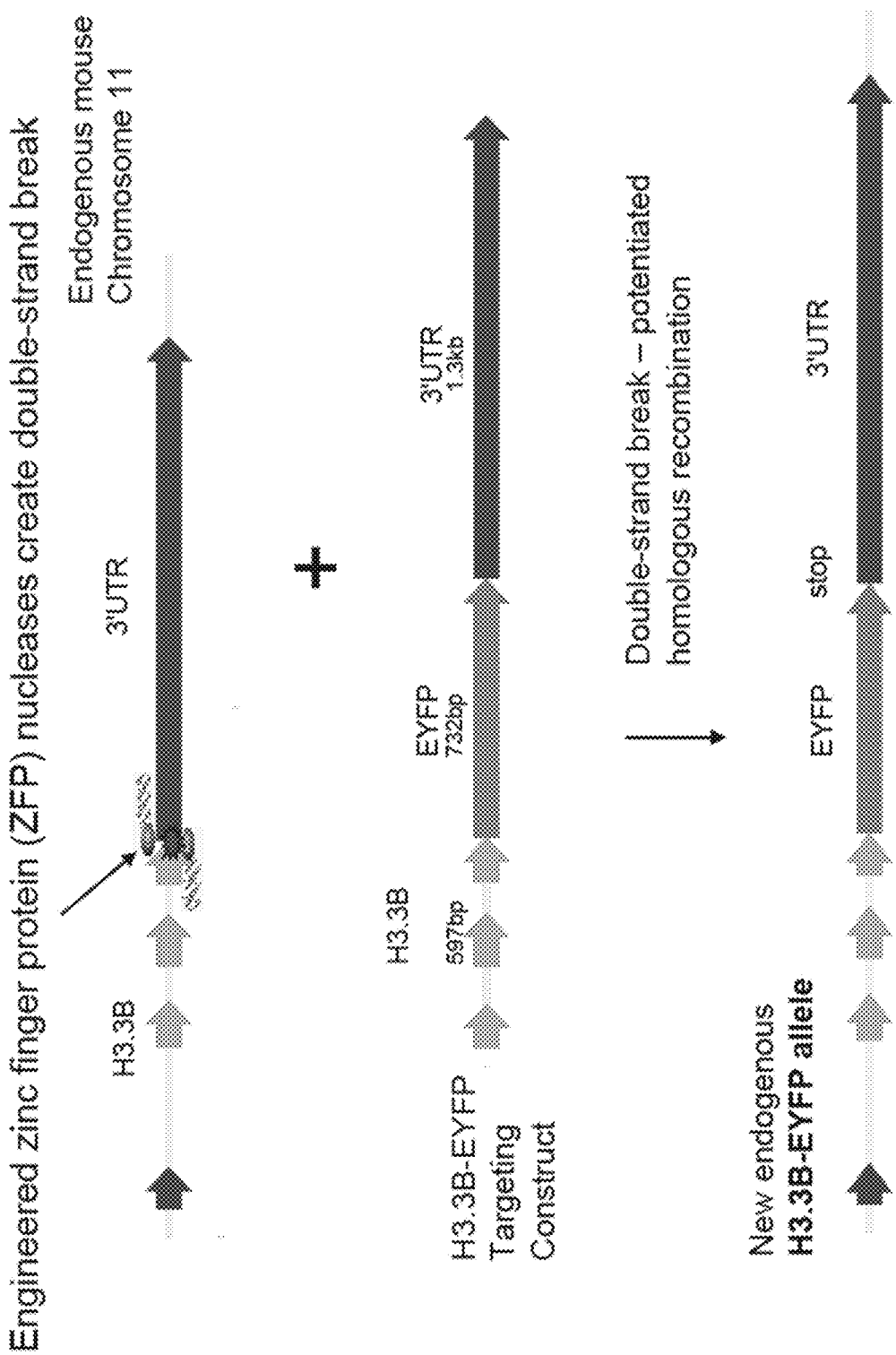
FIG. 2 depicts the scheme for introducing a fluorescent protein (enhanced yellow fluorescent protein (EYFP)) into the 3' untranslated region of the murine histone H3.3B gene. The top line shows the schematic of the H3.3B gene in the murine genome on chromosome 11 and shows the target site on the gene sequence for the H3.3B-specific ZFN. The second line depicts the donor nucleotide ("targeting construct") comprising a H3.3B gene linked to a EYFP sequence where the EYFP has been inserted at the 5' end of the 3' untranslated region. The bottom line depicts the insertion of the donor nucleotide into the H3.3B locus in the murine genome.
Figure 3A:
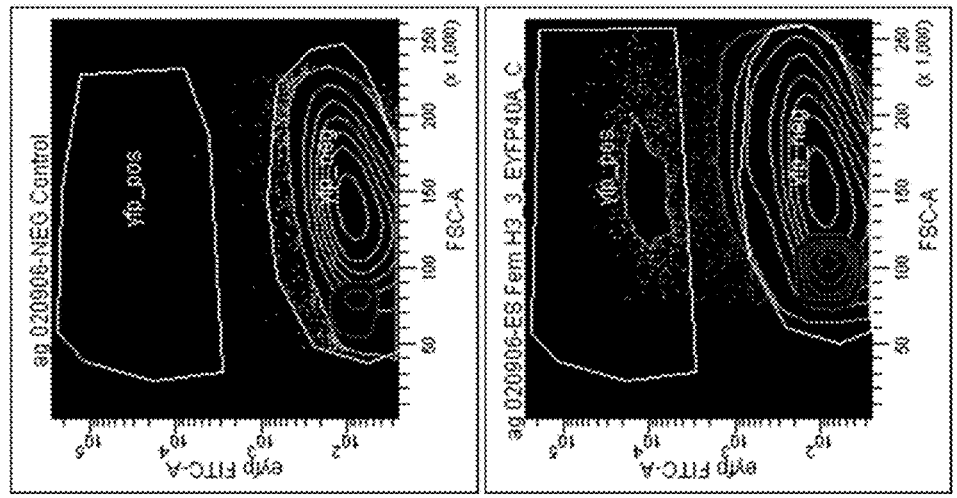
FIGS. 3A and 3B depicts the results from FACS and Southern blot analysis demonstrating the heterozygous integration of the EYFP transgene into murine ES cells.
Figure 3B:
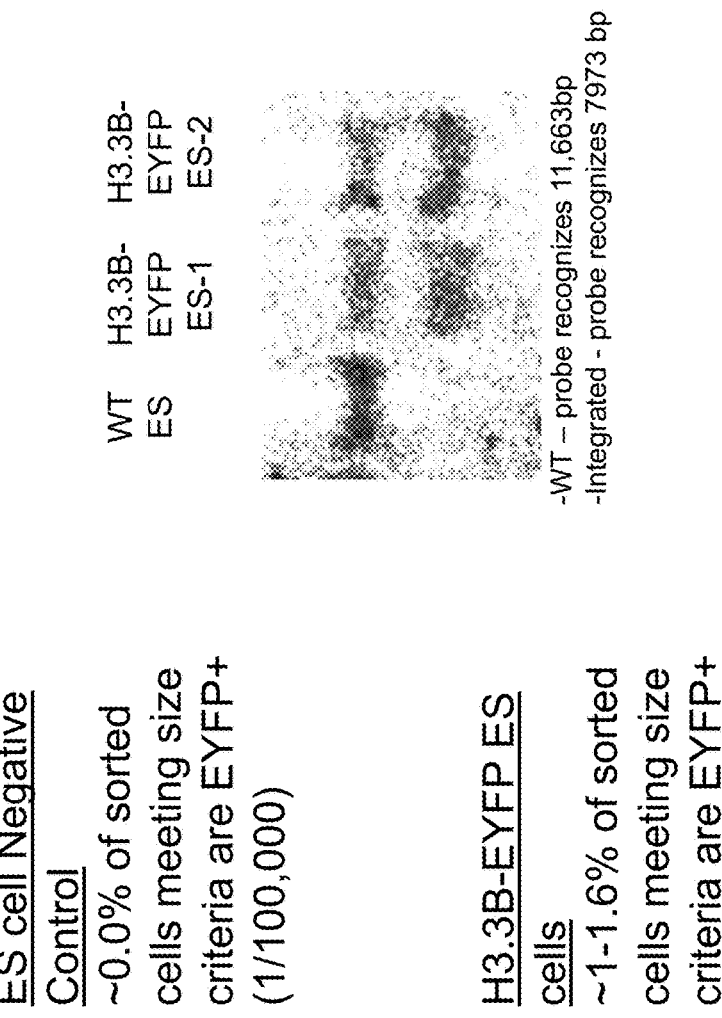

Described herein are homozygously modified organisms, including knockout (KO) organisms with no added genetic material at either allele of targeted locus and knock-in organisms that include transgenes of interest, but in which the transgene of interest lacks sequences encoding a reporter such as selectable marker. Also described are methods of generating these modified organisms. In particular, the organisms typically have modifications that alter gene function at both alleles. These organisms are generated by providing cells from the organism of interest, using nucleases to insert an exogenous reporter sequence (e.g., screening or selectable marker) via targeted integration (TI) into an allele at a selected locus in the cell, identifying cells in which the exogenous reporter sequence was inserted into an allele at the selected locus, screening the mono-allelic reporter-TI clones for modification events at the second allele of the locus to identify cells with one reporter TI allele and in which the other allele is modified by NHEJ (reporter TI/NHEJ) or in which the other allele comprises a non-reporter marker transgene (reporter-TI/modified clones), allowing the reporter-TI/modified clones to develop to reproductively mature organisms, crossing the reporter-TI/modified organisms, and identifying progeny of the crosses that are biallelic knockout (NHEJ/NHEJ) or biallelic non-reporter marker knock-in (non-reporter TI/non-reporter marker TI) organisms.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "TAL-effector DNA binding domain" is a protein, or a domain within a larger protein, that interacts with DNA in a sequence-specific manner through one or more tandem repeat domains.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains (e.g., the recognition helix region) can be "engineered" to bind to a predetermined nucleotide sequence. The engineered region of the zinc finger is typically the recognition helix, particularly the portion of the alpha-helical region numbered −1 to +6. Backbone sequences for an engineered recognition helix are known in the art. See, e.g., Miller et al. (2007) Nat Biotechnol 25, 778-785. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see, also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; and International Patent Publication Nos. WO 95/19431; WO 96/06166; WO 98/53057; WO 98/54311; WO 00/27878; WO 01/60970; WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity.

The percent identity of two sequences, whether nucleic acid or amino acid sequences, is the number of exact matches between two aligned sequences divided by the length of the shorter sequences and multiplied by 100.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break (DSB) has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another. In some embodiments, two DSBs are introduced by the targeted nucleases described herein, resulting in the deletion of the DNA in between the DSBs. In some embodiments, the "donor" polynucleotides are inserted between these two DSBs.

Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528 and 2008/0131962, incorporated herein by reference in their entireties.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain or between a TAL-effector DNA binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA, shRNA, RNAi, miRNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, donor integration, random mutation) can be used to modulate expression. Gene inactivation refers to any reduction in gene expression as compared to a cell that does not include a modifier as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soybean, canola (rapeseed), and alfalfa. Plant cells may be from any part of the plant and/or from any stage of plant development.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions.

Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably in a routine assay. Suitable reporter genes for particular species will be known to the skilled artisan and include, but are not limited to, Mel1, chloramphenicol acetyl transferase (CAT), light generating proteins such as GFP, luciferase and/or β-galactosidase. Suitable reporter genes for animals may also encode markers or enzymes that can be measured in vivo such as thymidine kinase, measured in vivo using PET scanning, or luciferase, measured in vivo via whole body luminometric imaging. Selectable markers can also be used instead of, or in addition to, reporters. Positive selection markers are those polynucleotides that encode a product that enables only cells that carry and express the gene to survive and/or grow under certain conditions. For example, cells that express neomycin resistance ($Neo^r$) gene are resistant to the compound G418, while cells that do not express $Neo^r$ are skilled by G418. Likewise, plant cells that express an herbicide tolerance (resistance) gene (e.g., PAT (phosphinothricin acetyl transferase) gene), which confers resistance to the herbicide bialaphos. Other examples of positive selection markers including hygromycin resistance and the like will be known to those of skill in the art. Negative selection markers are those polynucleotides that encode a product that enables only cells that carry and express the gene to be killed under certain conditions. For example, cells that express thymidine kinase (e.g., herpes simplex virus thymidine kinase, HSV-TK) are killed when gancyclovir is added. Other negative selection markers are known to those skilled in the art. The selectable marker need not be a transgene and, additionally, reporters and selectable markers can be used in various combinations.

Overview

Described herein are compositions and methods for generating homozygously modified, including knock-out (KO) organisms without inserted exogenous sequences such as selectable markers and organisms containing a transgene without sequences encoding reporters (e.g., selectable markers) at both alleles of the desired locus. The organisms are typically generated in two steps. In the first step, one or more nucleases (e.g., ZFNs) are used for targeted integration (TI) of a heterologous, donor-derived sequence of interest into the desired locus in the cell. The heterologous sequence typically contains a reporter (e.g., selectable or screening marker) that allows for selection of clones with a reporter-TI at one allele of the locus of interest. For TI of a transgene, a desired transgene donor (lacking reporter sequences) is co-introduced with the reporter donor. The reporter-TI-selected clones are then genotyped at the non-reporter-TI allele to identify cells in which the non-reporter-TI allele is disrupted by NHEJ, or to identify cells that contain the non-reporter marker transgene inserted at the non-reporter-TI allele.

In a second step, the reporter-TI/modified clones (e.g., reporter-TI/NHEJ or reporter-TI/non-reporter TI clones) identified as above are allowed to develop to reproductive maturity and then these reporter-TI/modified heterozygous organisms are crossed to each other or self crossed. One-quarter of the progeny of the reporter-TI/modified organisms from these crosses are expected to be homozygous for the modified events (NHEJ/NHEJ or non-reporter TI/non-reporter TI), thus providing homozygously modified organisms without any inserted reporter DNA.

Nucleases

The methods and compositions described herein are broadly applicable and may involve any nuclease of interest. Non-limiting examples of nucleases include meganucleases, zinc finger nucleases and TALENs. The nuclease may comprise heterologous DNA-binding and cleavage domains (e.g., zinc finger nucleases; meganuclease DNA-binding domains with heterologous cleavage domains or TALENs) or, alternatively, the DNA-binding domain of a naturally-occurring nuclease may be altered to bind to a selected target site (e.g., a meganuclease that has been engineered to bind to site different than the cognate binding site).

In certain embodiments, the nuclease is a meganuclease (homing endonuclease). Naturally-occurring meganucleases recognize 15-40 base-pair cleavage sites and are commonly grouped into four families: the LAGLIDADG family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

DNA-binding domains from naturally-occurring meganucleases, primarily from the LAGLIDADG family, have been used to promote site-specific genome modification in plants, yeast, *Drosophila*, mammalian cells and mice, but this approach has been limited to the modification of either homologous genes that conserve the meganuclease recognition sequence (Monet et al. (1999), *Biochem. Biophysics. Res. Common.* 255: 88-93) or to pre-engineered genomes into which a recognition sequence has been introduced (Route et al. (1994), *Mol. Cell. Biol.* 14: 8096-106; Chilton et al. (2003), *Plant Physiology.* 133: 956-65; Puchta et al. (1996), *Proc. Natl. Acad. Sci. USA* 93: 5055-60; Rong et al. (2002), *Genes Dev.* 16: 1568-81; Gouble et al. (2006), *J. Gene Med.* 8(5):616-622). Accordingly, attempts have been made to engineer meganucleases to exhibit novel binding specificity at medically or biotechnologically relevant sites (Porteus et al. (2005), *Nat. Biotechnol.* 23: 967-73; Sussman et al. (2004), *J. Mol. Biol.* 342: 31-41; Epinat et al. (2003), *Nucleic Acids Res.* 31: 2952-62; Chevalier et al. (2002) *Molec. Cell* 10:895-905; Epinat et al. (2003) *Nucleic Acids Res.* 31:2952-2962; Chames et al. (2005) *Nucleic Acids Res* 33(20):e178; Arnould et al. (2006) *J. Mol. Biol.* 355:443-458; Ashworth et al. (2006) *Nature* 441:656-659; Paques et al. (2007) *Current Gene Therapy* 7:49-66; U.S. Patent Publication Nos. 20070117128; 20060206949; 20060153826; 20060078552; and 20040002092). In addition, naturally-occurring or engineered DNA-binding domains from meganucleases have also been operably linked with a cleavage domain from a heterologous nuclease (e.g., FokI).

The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like (TAL) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. Vesicatoria (see Bonas et al (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the code for DNA recognition of these TAL-effectors has been determined such that an HD sequence at positions 12 and 13 leads to a binding to cytosine (C), NG binds to T, NI to A, C, G or T, NN binds to A or G, and IG binds to T. These DNA binding repeats have been assembled into proteins with new combinations and numbers of repeats, to make artificial transcription factors that are able to interact with new sequences and activate the expression of a reporter gene in plant cells (Boch et al, ibid). However, these DNA binding domains have not been shown to have general applicability in the field of targeted genomic editing or targeted gene regulation in all cell types. In particular, Boch et al showed function in plant cells only (namely, in the biological setting for which these domains have evolved to function in) and did not demonstrate activity at an endogenous locus. Moreover, engineered TAL-effectors have not been shown to function in association with any exogenous functional protein effector domains (nuclease, transcription factor, regulatory, enzymatic, recombinase, methylase, and/or reporter domains) not naturally found in natural *Xanthomonas* TAL-effector proteins in mammalian cells. In a recent publication by Christian et al ((2010)<Genetics epub 10.1534/genetics.110.120717), engineered TAL proteins were linked to a FokI cleavage half domain to yield a TAL effector domain nuclease fusion (TALEN) and were shown to be active in a yeast reporter assay where cleavage of the plasmid based target is require for the assay.

In other embodiments, the nuclease is a zinc finger nuclease (ZFN). ZFNs comprise a zinc finger protein that has been engineered to bind to a target site in a gene of choice and cleavage domain or a cleavage half-domain.

Zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453, 242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; ZFNs and methods for design and construction of fusion proteins (and polynucleotides encoding same) are known to those of skill in the art and described in detail in U.S. Patent Publication Nos. 20050064474 and 20060188987, incorporated by reference in their entireties herein.

In addition, as disclosed in these and other references, zinc finger domains and/or multi-fingered zinc finger proteins may be linked together using any suitable linker sequences, including for example, linkers of 5 or more amino acids in length. See, e.g., U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Nucleases such as ZFNs, TALENs and/or meganucleases also comprise a nuclease (cleavage domain, cleavage half-domain). As noted above, the cleavage domain may be heterologous to the DNA-binding domain, for example a zinc finger DNA-binding domain and a cleavage domain from a nuclease or a meganuclease DNA-binding domain or a TAL-effector domain and a cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474 and 20060188987 and in U.S. Publication No. US-2008-0131962-A1, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gin (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes.

The engineered cleavage half-domains described herein are obligate heterodimer mutants in which aberrant cleavage is minimized or abolished. See, e.g., Example 1 of WO 07/139898. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. Pat. No. 8,962, 281).

Engineered cleavage half-domains described herein can be prepared using any suitable method, for example, by site-directed mutagenesis of wild-type cleavage half-domains (Fok I) as described in U.S. Patent Publication Nos. 20050064474 and 20080131962.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases (e.g., ZFNs) can be screened for activity prior to use, for example in a yeast-based chromosomal system as described in WO 2009/042163 and 20090068164.

Expression Vectors

A nucleic acid encoding one or more nucleases can be cloned into a vector for transformation into prokaryotic or eukaryotic cells. Vectors can be prokaryotic vectors, e.g., plasmids, or shuttle vectors, insect vectors, or eukaryotic vectors, including plant vectors described herein.

Nuclease expression constructs can be readily designed using methods known in the art. See, e.g., United States Patent Publications 20030232410; 20050208489; 20050026157; 20050064474; 20060188987; 20060063231; 20080182332; 2009011188 and International Publication WO 07/014275. Expression of the nuclease may be under the control of a constitutive promoter or an inducible promoter, for example the galactokinase promoter which is activated (de-repressed) in the presence of raffinose and/or galactose and repressed in presence of glucose. Non-limiting examples of plant promoters include promoter sequences derived from *A. thaliana* ubiquitin-3 (ubi-3) (Callis, et al., 1990, *J. Biol. Chem.* 265-12486-12493); *A. tumifaciens* mannopine synthase (Δmas) (Petolino et al., U.S. Pat. No. 6,730,824); and/or Cassava Vein Mosaic Virus (CsVMV) (Verdaguer et al., (1996) *Plant Molecular Biology* 31:1129-1139). Additional suitable bacterial and eukaryotic promoters are well known in the art and described, e.g., in Sambrook et al., *Molecular Cloning, A Laboratory Manual* (2nd ed. 1989; 3$^{rd}$ ed., 2001); Kriegler, *Gene Transfer and Expression: A Laboratory Manual* (1990); and *Current Protocols in Molecular Biology* (Ausubel et al., supra. Bacterial expression systems for expressing the ZFP are available in, e.g., *E. coli, Bacillus* sp., and *Salmonella* (Palva et al. (1983) *Gene* 22:229-235).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to a nucleic acid sequence encoding the nuclease, and signals required, e.g., for efficient polyadenylation of the transcript, transcriptional termination, ribosome binding sites, or translation termination. Additional elements of the cassette may include, e.g., enhancers, heterologous splicing signals, and/or a nuclear localization signal (NLS).

Kits for such expression systems are commercially available. Eukaryotic expression systems for mammalian cells, yeast, plant and insect cells are well known by those of skill in the art and are also commercially available.

Any of the well known procedures for introducing foreign nucleotide sequences into such host cells may be used. These include the use of calcium phosphate transfection, polybrene, protoplast fusion, electroporation, ultrasonic methods (e.g., sonoporation), liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

DNA constructs may be introduced into (e.g., into the genome of) a desired plant host by a variety of conventional techniques. For reviews of such techniques see, for example, Weissbach & Weissbach *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9.

For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al (1987) *Nature* 327:70-73). Alternatively, the DNA constructs may be combined with suitable T-DNA flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al (1984) *Science* 233:496-498, and Fraley et al (1983) *Proc. Nat'l. Acad. Sci. USA* 80:4803.

In addition, gene transfer may be achieved using non-*Agrobacterium* bacteria or viruses such as *Rhizobium* sp. NGR234, *Sinorhizoboium meliloti*, *Mesorhizobium loti*, potato virus X, cauliflower mosaic virus and cassava vein mosaic virus and/or tobacco mosaic virus, See, e.g., Chung et al. (2006) *Trends Plant Sci.* 11(1):1-4.

The virulence functions of the *Agrobacterium tumefaciens* host will direct the insertion of the construct and adjacent marker into the plant cell DNA when the cell is infected by the bacteria using binary T DNA vector (Bevan (1984) *Nuc. Acid Res.* 12:8711-8721) or the co-cultivation procedure (Horsch et al (1985) *Science* 227:1229-1231). Generally, the *Agrobacterium* transformation system is used to engineer dicotyledonous plants (Bevan et al (1982) *Ann. Rev. Genet* 16:357-384; Rogers et al (1986) *Methods Enzymol.* 118:627-641). The *Agrobacterium* transformation system may also be used to transform, as well as transfer, DNA to monocotyledonous plants and plant cells. See U.S. Pat. No. 5,591,616; Hernalsteen et al (1984) *EMBO J* 3:3039-3041; Hooykass-Van Slogteren et al (1984) *Nature* 311:763-764; Grimsley et al (1987) *Nature* 325:1677-179; Boulton et al (1989) *Plant Mol. Biol.* 12:31-40; and Gould et al (1991) *Plant Physiol.* 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618).

Administration of effective amounts is by any of the routes normally used for introducing nucleases into ultimate contact with the cell to be treated. The nucleases are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Carriers may also be used and are determined in part by the particular composition being administered, as well as by the particular method used to administer the composition. Accordingly, there is a wide variety of suitable formulations of pharmaceutical compositions that are available (see, e.g., *Remington's Pharmaceutical Sciences*, 17$^{th}$ ed. 1985).

Organisms

The present invention is applicable to any organism in which it is desired to create a homozygously modified organism, including but not limited to eukaryotic organisms such as plants, animals (e.g., mammals such as mice, rats, primates, farm animals, rabbits, etc.), fish, and the like. Typically, the organisms are generated using isolated cells from the organism that can be genetically modified as described herein and can develop into reproductively mature organisms. Eukaryotic (e.g., yeast, plant, fungal, piscine and mammalian cells such as feline, canine, murine, bovine, and porcine) cells can be used. Cells from organisms containing one or more homozygous KO loci as described herein or other genetic modifications can also be used.

Exemplary mammalian cells include any cell or cell line of the organism of interest, for example oocytes, K562 cells, CHO (Chinese hamster ovary) cells, HEP-G2 cells, BaF-3 cells, Schneider cells, COS cells (monkey kidney cells expressing SV40 T-antigen), CV-1 cells, HuTu80 cells, NTERA2 cells, NB4 cells, HL-60 cells and HeLa cells, 293 cells (see, e.g., Graham et al. (1977) *J. Gen. Virol.* 36:59), and myeloma cells like SP2 or NS0 (see, e.g., Galfre and Milstein (1981) *Meth. Enzymol.* 73(B):3 46). Peripheral blood mononucleocytes (PBMCs) or T-cells can also be used, as can embryonic and adult stem cells. For example, stem cells that can be used include embryonic stem cells (ES), induced pluripotent stem cells (iPSC), mesenchymal stem cells, hematopoietic stem cells, muscle stem cells, skin stem cells and neuronal stem cells.

Exemplary target plants and plant cells include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., *petunia*, rose, *chrysanthemum*), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera Asparagus, *Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna,* and *Zea.* The term plant cells include isolated plant cells as well as whole plants or portions of whole plants such as seeds, callus, leaves, roots, etc. The present disclosure also encompasses seeds of the plants described above wherein the seed has the transgene or gene construct. The present disclosure further encompasses the progeny, clones, cell lines or cells of the transgenic plants described above wherein said progeny, clone, cell line or cell has the transgene or gene construct.

Targeted Integration

The first step in generating homozygously modified organisms as described herein involves nuclease-mediated targeted integration of a donor (exogenous) reporter sequence at the desired target locus. Specifically, the disclosed nucleases can be used to cleave DNA at a region of interest in cellular chromatin (e.g., at a desired or predetermined site in a genome). For such targeted DNA cleavage, the DNA binding domain of a nuclease (e.g., zinc finger binding domain) is engineered to bind a target site at or near the predetermined cleavage site, and a fusion protein comprising the DNA binding domain and a cleavage domain is expressed in a cell. Upon binding of the DNA-binding domain (e.g., zinc finger portion) of the fusion protein to the target site, the DNA is cleaved near the target site by the cleavage domain.

Alternatively, two fusion proteins, each comprising a zinc finger binding domain and a cleavage half-domain, are expressed in a cell, and bind to target sites which are juxtaposed in such a way that a functional cleavage domain is reconstituted and DNA is cleaved in the vicinity of the target sites. In one embodiment, cleavage occurs between the target sites of the two zinc finger binding domains. One or both of the zinc finger binding domains can be engineered.

Targeted cleavage by nucleases as described herein has been shown to result in targeted integration of a donor (exogenous) sequence (via homology-directed repair) at the site of cleavage. See, e.g., U.S. Patent Publication Nos. 2007/0134796, 2008/029580, 2008/0182332, 2009/0117617, and 2009/0111188.

Thus, in addition to the nucleases described herein, targeted replacement (integration) of a selected genomic sequence also requires the introduction of the replacement (or donor) reporter sequence. The donor reporter sequence can be introduced into the cell prior to, concurrently with, or subsequent to, expression of the fusion protein(s). The donor reporter polynucleotide generally contains sufficient homology to a genomic sequence to support homologous recombination (or homology-directed repair) between it and the genomic sequence to which it bears homology. It will be readily apparent that the donor sequences are typically not identical to the genomic sequence that they replace. For example, the sequence of the donor polynucleotides can contain one or more single base changes, insertions, deletions, inversions or rearrangements with respect to the genomic sequence, so long as sufficient homology with chromosomal sequences is present.

In certain embodiments, introduction of a desired transgene may also be accomplished. The desired transgene donor sequences will also have sufficient homology to the genomic sequence to support homologous recombination or homology-directed repair between it and the genomic sequence to which it has homology. See, e.g., U.S. Patent Publication No. US-2009-0263900-A1. Donor transgenes of interest typically contain sequences encoding a sequence of interest. Non-limiting examples include gene regulator sequences (e.g. promoter sequences), sequences encoding a protein product (e.g. proteins involved in phenotypic modification of the organism or a therapeutic protein) or sequences encoding a RNA product such as a shRNA, RNAi etc.

The donor reporter sequence typically includes a sequence encoding a reporter gene for identification of cells in which targeted integration has occurred. Any reporter gene can be used. In certain embodiments, the reporter gene provides a directly detectable signal directly, for example, a signal from a fluorescent protein such as, for example, GFP (green fluorescent protein). Fluorescence is detected using a variety of commercially available fluorescent detection systems, including, e.g., a fluorescence-activated cell sorter (FACS) system.

Reporter genes may also be enzymes that catalyze the production of a detectable product (e.g. proteases, nucleases, lipases, phosphatases, sugar hydrolases and esterases). Non-limiting examples of suitable reporter genes that encode enzymes include, for example, MEL1, CAT (chloramphenicol acetyl transferase; Alton and Vapnek (1979) *Nature* 282:864 869), luciferase, β-galactosidase, β-glucuronidase, β-lactamase, horseradish peroxidase and alkaline phosphatase (e.g., Toh, et al. (1980) *Eur. J. Biochem.* 182:231 238; and Hall et al. (1983) *J. Mol. Appl. Gen.* 2:101).

Additional reporter genes include selectable markers (e.g., positive and/or negative selection markers), including but not limited to antibiotic resistance such as ampicillin resistance, neomycin resistance, G418 resistance, puromycin resistance as well as herbicide resistance such a PAT gene.

The donor polynucleotides (reporter and/or transgene) can be DNA or RNA, single-stranded or double-stranded and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. A polynucleotide can be introduced into a cell as part of a vector molecule having additional sequences such as, for example, replication origins, promoters and genes encoding antibiotic or herbicide resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus).

Cells can be assayed for targeted integration in any suitable way, including by examination (sequencing or PCR) or the selected locus or by selecting and/or screening the treated cells for traits encoded by the marker genes present on the donor DNA. For instance, selection may be performed by growing the engineered cells on media containing an inhibitory amount of the antibiotic or herbicide to which the transforming gene construct confers resistance. Further, transformed cells may also be identified by screening for the activities of any visible marker genes (e.g., fluorescent proteins, β-glucuronidase, luciferase, B or C1 genes) that may be present on the recombinant nucleic acid constructs. Such selection and screening methodologies are well known to those skilled in the art.

Physical and biochemical methods also may be used to identify cells containing the donor sequences inserted into the targeted locus. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the amount of mRNA has increased, it can be assumed that the corresponding endogenous gene is being expressed at a greater rate than before. Other methods of measuring gene and/or CYP74B activity can be used. Different types of enzymatic assays can be used, depending on the substrate used and the method of detecting the increase or decrease of a reaction product or by-product. In addition, the levels of and/or CYP74B protein expressed can be measured immunochemically, i.e., ELISA, RIA, EIA and other antibody based assays well known to those of skill in the art, such as by electrophoretic detection assays (either with staining or western blotting).

Generating Homozygously Modified Organisms

Cells into which the reporter donor sequence has been inserted into the target locus are then assayed for the presence of modifications at the non-reporter-TI allele, for example NHEJ events or insertion of a transgene lacking sequences encoding a reporter (selectable marker). Such reporter-TI/modified cells can be identified using any suitable method known to the skilled artisan, including sequencing, PCR analysis and the like.

Subsequently, the reporter-TI/modified mutants are cultured or otherwise treated such that they generate a whole organism with reporter-TI/modified genotype at the desired locus. For example, traditional methods of pro-nuclear injection or oocyte injection can be used to generate reporter-TI/modified animals. See, e.g., U.S. Pat. No. 9,206,404 showing germline transmission of ZFN-modified rat oocytes.

Likewise, reporter-TI/modified plant cells can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al (1987) *Ann. Rev. of Plant Phys.* 38:467-486. One of skill in the art will recognize that after the expression cassette is stably incorporated in transgenic plants and confirmed to be operable, it can be introduced into other plants by sexual crossing. Any of a number of standard breeding techniques can be used, depending upon the species to be crossed. Further still, haploid organisms (e.g. gametophytes) may be created following meiosis of the transgenic organism. There are several organisms such as algae, fungi and some plants that are able to live at least part of their lifecycle in a haploid state.

Once the reporterTI/modified heterozygous organisms reach reproductive maturity, they can be crossed to each other, or in some instances, spores may be grown into haploids. Of the resulting progeny from crosses, approximately 25% will be homozygous modified/modified (NHEJ/NHEJ or non-reporter TI/non-reporter TI) at the target locus. Half of the haploid offspring will contain the modification of interest. The modified/modified organisms can be identified using any of the methods described above, including, but not limited to sequencing, PCR analysis and the like. These organisms will have the desired homozygous gene modification, but will not include any inserted exogenous reporter sequences (e.g., markers).

Kits

Also provided are kits for generating organisms as described herein. The kits typically contain polynucleotides encoding one or more nucleases and/or donor polynucleotides (e.g., with selectable markers) as described herein as well as instructions for analyzing selected TI clones for modifications at the non-reporter-TI allele and instructions for crossing the reporter-TI/modified organisms to each other to generate organisms that are homozygous at the disrupted locus without any inserted donor DNA into which the nucleases and/or donor polynucleotide are introduced. The kits can also contain cells, reagents, buffers for transformation of cells, culture media for cells, and/or buffers for performing assays. Typically, the kits also contain a label which includes any material such as instructions, packaging or advertising leaflet that is attached to or otherwise accompanies the other components of the kit.

Applications

The homozygously modified organisms described herein can be used for any application in which KO organisms with inserted exogenous sequences are currently used. Such organisms find use in biological and medical research, production of pharmaceutical drugs, experimental medicine, and agriculture.

For example, KO animals have proved very useful in analyzing the function of gene products and creating models for human diseases, thereby allowing drug discovery. Similarly, KO plants as described herein can be used to create crops with the desired genes disrupted but without the inserted sequences that potentially could damage native crops. Thus, KO plants as described herein can be non-transgenic GMOs in the sense that they do not include exogenous DNA. Alternatively, the KO organisms can lack inserted sequences at the disrupted locus (loci) but include transgenes at another locus or loci.

Creating plants or animals that are homozygous for a transgene but lack a exogenous reporter sequence is often desirable. Thus, methods and compositions described herein provide tools for generation of plants and animals in which a desired (non-reporter) gene sequence has been inserted into both alleles but the resultant plant progeny do not contain any reporter sequences. For example, regulator sequences may be inserted to control (repress or activate) a specific gene of interest. Similarly, a transgene may be inserted into all the alleles of a locus of interest. The transgene may be inserted to knock out a particular gene where expression of the target gene is not desired.

The following Examples relate to exemplary embodiments of the present disclosure in which the nuclease comprises a zinc finger nuclease (ZFN). It will be appreciated that this is for purposes of exemplification only and that other nucleases can be used, for instance homing endonucleases (meganucleases) with engineered DNA-binding domains and/or fusions of naturally occurring or engineered homing endonucleases (meganucleases) DNA-binding domains and heterologous cleavage domains or TALENs.

EXAMPLES

Example 1: Generation of Bi-Allelic Knockout Plants

ZFNs targeted to the IPK1 gene in *Zea mays* were used for targeted insertion (TI) of a herbicide resistant gene (PAT). The ZFNs used and TI techniques are described in Shukla et al. (2009) *Nature* 459:437-441 and U.S. Patent Publication Nos. 20080182332 and 20090111188. As described, ZFNs precisely modified the target locus by mono-allelic or bi-allelic targeted integration of the selectable marker.

Subsequently, the TI/-(mono-allelic) clones (events) were genotyped at the non-TI allele. As shown in FIG. 1, an event of the events sequenced at the non-TI allele had a NHEJ-induced mutation (deletion) at the non-TI allele. FIG. 1 shows the wild type sequence and multiple sequence reads of the event. Such events are designated TI/NHEJ. TI/NHEJ events are then self pollinated by standard methods to obtain plants are that are bi-allelic knockouts (−/− or NHEJ/NHEJ) at the targeted locus, but are devoid of the inserted reporter (selectable marker) sequence.

Example 2: Generation of Heterozygote Knockout Murine Stem Cells

ZFNs targeted to the murine histone H3.3B were used for targeted integration of a fluorescent marker enhanced yellow fluorescent protein (EYFP) at the start of the 3' untranslated portion of this gene. The ZFNs were constructed essentially as described in U.S. Pat. No. 6,534,261. The recognition helices for the ZFN pair used as well as the target sequence are shown below in Tables 1 and 2.

TABLE 1

Murine H3.3B- targeted ZFNs

| SBS # | Design | | | |
|-------|--------|--------|--------|--------|
|       | F1 | F2 | F3 | F4 |
| 7269 | RSDHLSE (SEQ ID NO: 1) | RNDTRKT (SEQ ID NO: 2) | QSSNLAR (SEQ ID NO: 3) | RSDDRKT (SEQ ID NO: 4) |
| 7270 | DRSALSR (SEQ ID NO: 5) | TSANLSR (SEQ ID NO: 6) | RSDVLSE (SEQ ID NO: 7) | QRNHRTT (SEQ ID NO: 8) |

TABLE 2

Target sites for H3.3B ZFNs

| SBS # | Target Site |
|-------|-------------|
| 7269 | cgCCGGATACGGGGag (SEQ ID NO: 9) |
| 7270 | gcCAACTGGATGTCtt (SEQ ID NO: 10) |

A donor DNA was constructed containing the H3.3B gene operably linked to the EYFP sequence (see FIG. 2). Briefly, a PCR fragment of genomic DNA from mouse H3.3B was cloned out of a genomic bacterial artificial chromosome (BAC) from C57BL/6J mouse chromosome 11 using Phusion polymerase (NEB F-530L) and into a pCR2.1 vector (pCR2.1-H3.3B) using TA-TOPO cloning (Invitrogen K4500-02). To generate the H3.3B-EYFP donor construct (pCR2.1-H3.3B-EYFP), a 6 amino acid (SRPVAT) linker followed by the open-reading frame of EYFP (Clontech) was inserted in-frame into the last coding exon of H3.3B. The H3.3B-EYFP donor included no H3.3B promoter sequence, containing approximately 0.6 kb of 5' homologous genomic sequence starting at the second H3.3B codon, including introns, until the last H3.3B coding amino acid, followed by the linker and EYFP, a stop codon, and approximately 1.3 kb homologous to the H3.3B 3'UTR. The donor and the expression vector containing the ZFN pair were then co-transfected into mouse embryonic stem cells. To deliver ZFNs and donor constructs, mouse ES cells were transfected by Amaxa nucleofection. In brief, immediately prior to transfection, ES cells were feeder depleted by harvesting the ES cells, plating on a feeder-free dish for 30 min, and then collecting the ES enriched non-adherent cells for transfection. 2-5*10^6 cells ES cells were resuspended in 90 µl solution, mixed with two non-linearized plasmids (1 µg of ZFN plasmid with both ZFNs separated by a 2A peptide sequence+10 µg of donor plasmid) in 10 µl nucleofection solution, and transfected using program A-013 as described in the Amaxa manufacturer's protocol for mouse ES cells.

Following transfection, sterile plastic pipettes were used to transfer the cells to warm ES media in tissue culture dishes that were already prepared with feeders. After transfer, ES cells were cultured in standard conditions on treated feeders for 3-5 days prior to fluorescent activated cell sorting (FACS) or fluorescent colony picking. Following colony picking, clonal isolation and expansion, genomic DNA was prepared using the Qiagen DNeasy Blood & Tissue Kit (Qiagen 69504). Individual clones were screened by PCR. PCR products from both wild-type and modified H3.3B alleles were sequenced using standard methods. To perform Southern blotting, genomic DNA was digested from wild-type and targeted ES cells with BsrBI, and used a labeled 638 bp AvaII fragment of the H3.3B donor as probe to visualize wild-type H3.3B and integrated H3.3B donors.

FACS and Southern blot analysis confirmed that the EYFP had been integrated into the H3.3B locus (see FIG. 6). Approximately 20% of the clones that contained an EYFP integrated in one H3.3B locus were found to have had an NHEJ event at the other locus (see FIG. 7).

Example 3: Generation of Homozygote Knockout Mice

The stem cells containing the heterozygous reporter TI/modified alleles at the locus of interest are used to generate homozygous modified/modified mice using standard protocols (for example see *Manipulating the Mouse Embryo, A Laboratory Manual*, 3$^{rd}$ *Edition* Nagy et al, eds. Cold Spring Harbor Laboratory Press (2003)).

Example 4: Generation of Heterozygotic Mammalian Cells Containing a Transgene Heterozygous cells are generated wherein one allele of the PPP1R12C gene (see U.S. Patent Publication No. 20080299580) contains the PGK-GFP-pA selectable marker, and the other allele contains a transgene carrying a novel RFLP in the PPP1R12C gene that creates a Hind III restriction site. Briefly, K562 cells are transfected with the ZFN expression plasmids as described above along with the two donor molecules. One donor comprises the reporter GFP driven by the PGK promoter, and the other donor comprises a PPP1R12C gene with the novel RFLP. GFP positive cells are isolated by limiting dilution and visual inspection. Clones are grown up and genomic DNA is isolated for genotyping by PCR and sequencing.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of generating a homozygous knockout Zea mays plant, the method comprising:
   (a) introducing into isolated Zea mays cells:
      (i) one or more polynucleotides encoding a pair of zinc finger nucleases (ZFNs) that cleave a Zea mays inositol-pentakisphosphate 2-kinase (IPK1) gene, each zinc finger nuclease comprising a cleavage domain and a zinc finger protein (ZFP) DNA-binding domain that binds to a target site in the IPK1 gene, wherein the ZFP comprises multiple zinc fingers, and each zinc finger comprises a recognition helix region; and
      (ii) a donor nucleic acid sequence encoding an herbicide resistance protein flanked by regions of homology to the IPK1 gene;
   (b) identifying Zea mays cells comprising:
      (i) the donor nucleic acid sequence integrated into the first allele of the IPK1 gene; and
      (ii) a non-homologous end joining (NHEJ) modification in the second allele of the IPK1 gene, wherein the NHEJ modification comprises an insertion or deletion that disrupts expression of the IPK1 gene;
   (c) allowing the cells identified in step (b) to develop into reproductively mature Zea mays plants;
   (d) crossing the reproductively mature Zea mays plants to each other;
   (e) identifying Zea mays plants obtained from the crossing of step (d) that comprise the NHEJ modification that disrupts expression of the IPK1 gene in both the first and second allele of the IPK1 gene; and
   (f) selecting Zea mays plants obtained from step (e) that comprise a homozygous knockout of the IPK1 gene.

2. A method of generating a homozygous knock-in Zea mays plant, the method comprising:
   (a) introducing into isolated Zea mays cells:
      (i) one or more polynucleotides encoding a pair of zinc finger nucleases (ZFNs) that cleave a Zea mays inositol-pentakisphosphate 2-kinase (IPK1) gene, each zinc finger nuclease comprising a cleavage domain and a zinc finger protein (ZFP) DNA-binding domain that binds to a target site in the IPK1 gene, wherein the ZFP comprises multiple zinc fingers, and each zinc finger comprises a recognition helix region; and
      (ii) a first donor nucleic acid sequence encoding an herbicide resistance protein flanked by regions of homology to the IPK1 gene;
      (iii) a second donor nucleic acid sequence encoding a protein other than herbicide resistance protein flanked by regions of homology to the IPK1 gene;
   (b) identifying cells comprising:
      (i) the first donor nucleic acid sequence integrated into the first allele of the IPK1 gene; and
      (ii) the second donor nucleic acid sequence integrated into the second allele of the IPK1 gene, wherein the second donor nucleic acid sequence disrupts expression of the IPK1 gene;
   (c) allowing the cells identified in step (b) to develop into reproductively mature Zea mays plants;
   (d) crossing the reproductively mature Zea mays plants to each other; and
   (e) identifying Zea mays plants obtained from the crossing of step (d) that comprise the second donor nucleic acid sequence that disrupts expression of the IPK1 gene in both the first and second allele of the IPK1 gene; and
   (f) selecting plants obtained from step (e) that comprise a homozygous knock-in of the second donor nucleic acid sequence that disrupts expression of the IPK1 ene.

3. The method of claim 2, wherein the one or more polynucleotides encoding the pair of ZFNs, the first donor nucleic acid sequence, and the second donor nucleic acid sequence are introduced concurrently.

4. The method of claim 2, wherein the one or more polynucleotides encoding the pair of ZFNs, the first donor nucleic acid sequence, and the second donor nucleic acid sequence are introduced sequentially.

* * * * *